US008888796B2

(12) United States Patent
Lindh, Sr. et al.

(10) Patent No.: US 8,888,796 B2
(45) Date of Patent: Nov. 18, 2014

(54) DEVICES FOR TENSIONING BARBED SUTURES AND METHODS THEREFOR

(75) Inventors: David Lindh, Sr., Flemington, NJ (US); Jesse G. Nawrocki, Annandale, NJ (US); John P. Matonick, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 1059 days.

(21) Appl. No.: 12/135,176

(22) Filed: Jun. 7, 2008

(65) Prior Publication Data
US 2009/0306710 A1   Dec. 10, 2009

(51) Int. Cl.
*A61B 17/04* (2006.01)
*A61B 19/00* (2006.01)
*A61B 17/06* (2006.01)

(52) U.S. Cl.
CPC ..... *A61B 17/06166* (2013.01); *A61B 2019/464* (2013.01); *A61B 2017/06057* (2013.01); *A61B 17/0483* (2013.01); *A61B 2017/0496* (2013.01)
USPC ........................................................ 606/148

(58) Field of Classification Search
CPC ............... A61B 17/04; A61B 17/0482; A61B 17/0483; A61B 2017/0496
USPC .................. 606/139, 144, 148, 232
See application file for complete search history.

(56) References Cited

U.S. PATENT DOCUMENTS

| | | | |
|---|---|---|---|
| 3,633,582 A | 1/1972 | Steinman | |
| 4,164,225 A | 8/1979 | Johnson | |
| 5,234,444 A * | 8/1993 | Christoudias | 606/148 |
| 5,258,016 A * | 11/1993 | DiPoto et al. | 606/232 |
| 5,261,917 A | 11/1993 | Hasson et al. | |
| 5,282,809 A * | 2/1994 | Kammerer et al. | 606/148 |
| 5,292,327 A | 3/1994 | Dodd et al. | |
| 5,403,330 A | 4/1995 | Tuason | |
| 5,423,837 A | 6/1995 | Mericle et al. | |

(Continued)

FOREIGN PATENT DOCUMENTS

WO   9604854   2/1996

OTHER PUBLICATIONS

Murtha, A.P., Kaplan, A.L., Paglia, M.J., Mills, B.B., Feldstein, M.L., Ruff, G.L., "Evaluation of a novel technique for wound closure using barbed suture", (2006) Plastic and Reconstructive Surgery, 117 (6), pp. 1769-1780.

(Continued)

*Primary Examiner* — Melanie Tyson
(74) *Attorney, Agent, or Firm* — Doherty IP Law Group LLC

(57) ABSTRACT

A device for tensioning barbed sutures used for securing tissue or prosthetic devices includes a handle, and a shaft having a proximal end connected with the handle and a distal end remote therefrom. The distal end of the shaft includes a pressure applying surface for pressing against the tissue and the prosthetic devices. The tensioning device includes a pair of grooves extending through the shaft from the pressure applying surface at the distal end of the shaft toward the proximal end of the shaft. A barbed suture is tensioned by aligning a first section of the suture in the first groove and a second section of the suture in the second groove. After the first and second suture sections are aligned in the grooves, the proximal ends of the sections may be pulled for applying tension to the suture.

19 Claims, 12 Drawing Sheets

(56) References Cited

U.S. PATENT DOCUMENTS

| | | | |
|---|---|---|---|
| 5,507,756 A | 4/1996 | Hasson | |
| 5,549,618 A | 8/1996 | Fleenor et al. | |
| 5,562,684 A * | 10/1996 | Kammerer | 606/139 |
| 5,653,719 A * | 8/1997 | Raiken | 606/148 |
| D386,583 S | 11/1997 | Ferragamo et al. | |
| 5,769,863 A | 6/1998 | Garrison | |
| 5,797,929 A | 8/1998 | Andreas et al. | |
| 5,814,051 A | 9/1998 | Wenstrom | |
| 5,931,855 A | 8/1999 | Buncke | |
| 5,944,724 A | 8/1999 | Lizardi | |
| 5,948,019 A | 9/1999 | Shu et al. | |
| 6,283,979 B1 | 9/2001 | Mers Kelly et al. | |
| 6,358,259 B1 * | 3/2002 | Swain et al. | 606/148 |
| 6,511,488 B1 | 1/2003 | Marshall et al. | |
| 6,962,582 B2 * | 11/2005 | Zinkel | 606/1 |
| 7,048,748 B1 | 5/2006 | Ustuner | |
| 7,056,331 B2 | 6/2006 | Kaplan et al. | |
| 7,172,625 B2 | 2/2007 | Shu et al. | |
| 2002/0087178 A1 * | 7/2002 | Nobles et al. | 606/167 |
| 2003/0078600 A1 | 4/2003 | O'Quinn et al. | |
| 2003/0208210 A1 | 11/2003 | Dreyfuss et al. | |
| 2004/0060409 A1 * | 4/2004 | Leung et al. | 83/522.14 |
| 2004/0127887 A1 | 7/2004 | Zinkel | |
| 2006/0207608 A1 | 9/2006 | Hirotsuka et al. | |
| 2007/0005110 A1 | 1/2007 | Collier et al. | |
| 2007/0049952 A1 | 3/2007 | Weiss | |
| 2007/0257395 A1 | 11/2007 | Lindh et al. | |

OTHER PUBLICATIONS

Ruff, G., "Technique and uses for absorbable barbed sutures", (2006) Aesthetic Surgery Journal, 26 (5), pp. 620-628.

* cited by examiner

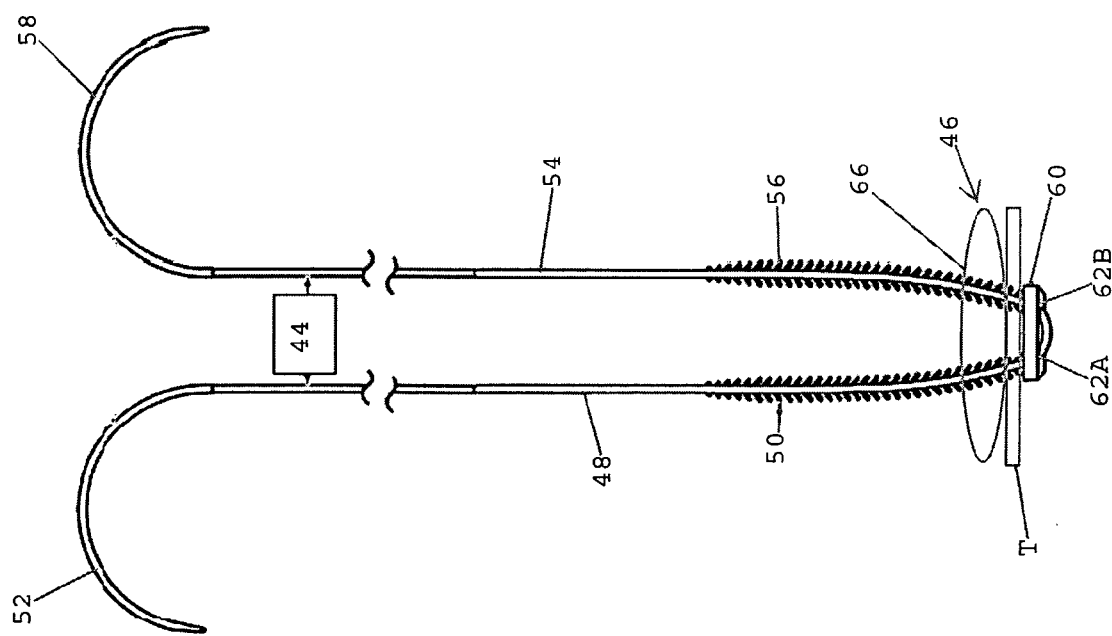

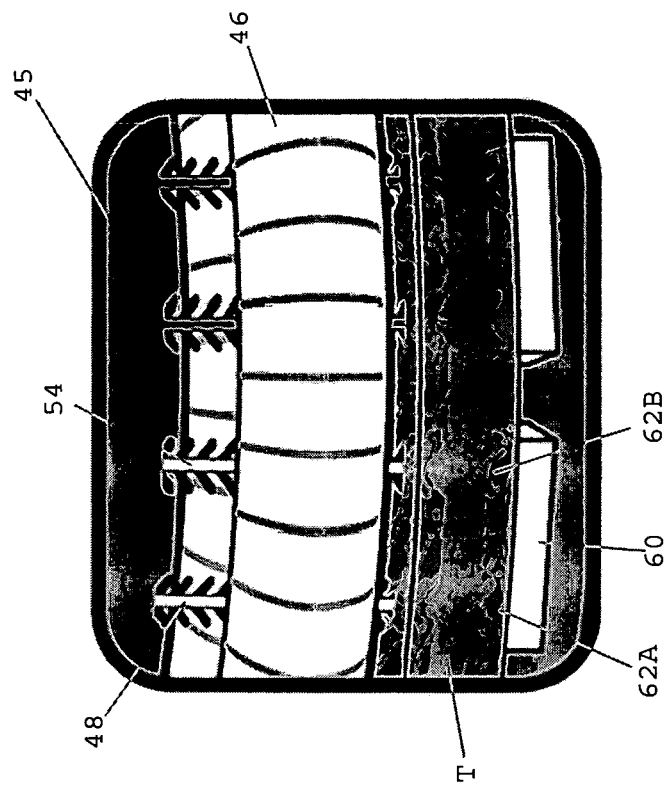
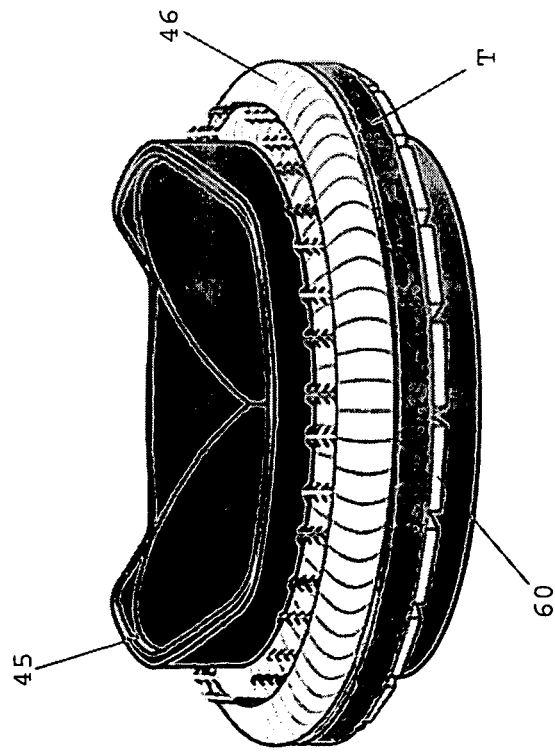
FIG. 4C
FIG. 4B

DEVICES FOR TENSIONING BARBED SUTURES AND METHODS THEREFOR

BACKGROUND OF THE INVENTION

1. Field of the Invention

The present invention generally relates to surgical sutures, and more specifically relates to barbed sutures and devices used for affixing barbed sutures to tissue and prosthetic devices.

2. Description of the Related Art

Surgical sutures are used to close wounds and surgical incisions, and to repair damaged or severed muscles, vessels, and tissue. Typically, the suture is attached at one end to a needle, and the needle is drawn through tissue to form one or more loops holding the tissue together. The suture is subsequently tied off in one or more knots so that the tissue will remain drawn together.

Although sutures are very effective for closing wounds, there are a number of problems associated with using conventional sutures. Many of these troubles are directly related to the knots used to secure sutures in place. If the knots are not tied properly, defects may arise including slippage, knot breakage, and re-opening of the wound. In addition, using knots to secure sutures may distort tissue, restrict blood flow, increase the formation of scars, impede wound healing, and result in infection.

In response to the deficiencies associated with conventional sutures, sutures having barbs have been developed. Unlike conventional sutures, barbed sutures have projecting barbs that allow the suture to be used to close wounds, approximate tissue, tighten tissue, and attach prosthetic devices without using knots. Fixing conventional sutures with knots requires the knots to be pushed down toward the tissue to assure proper tensioning and fixation of the sutures. In contrast, barbed sutures achieve proper tensioning and fixation by applying tension to the suture. For example, U.S. Pat. No. 5,931,885 discloses barbed sutures that are used for cosmetic procedures such as brow-lifts and face-lifts.

In some procedures, it is desirable to use barbed sutures to secure prosthetic devices such as bioprosthetic heart valves. For example, in certain embodiments of commonly assigned U.S. Published Patent Application No. 2007/0005110, the disclosure of which is hereby incorporated by reference herein, braided barbed sutures are disposed in a heart valve sewing ring by first passing the sutures through an annulus and then passing the sutures through the valve sewing ring. Approximately 12-20 sets of braided barbed sutures are placed to secure the valve in place. The valve sewing ring is then parachuted down the sets of barbed sutures and seated in place within the annulus. After the sewing ring has been parachuted in a downward direction, the barbs prevent the sewing ring from being moved in the opposite, upward direction. Thus, the barbs hold the sewing ring in place without requiring knots.

When fixing barbed sutures to tissue or prosthetic devices, surgeons often use the tips of their fingers or the distal ends of surgical instruments (e.g. forceps) to apply pressure on the tissue or the prosthetic devices. These techniques may result in damage to the tissue, poor visibility at the surgical site due to the surgical site being blocked by the fingers or the surgical instruments, and insufficient or improper tensioning of the barbed sutures in the tissue or prosthetic devices. Conventional techniques also require many different instruments to be brought together to secure the barbed sutures in place, which may prove cumbersome.

When the above-described devices and techniques are used for applying tension to a barbed suture, the tissue is frequently stretched forming a tent-like shape due to the elastic properties of the tissue. This stretching may result in tissue trauma and poor control over the resulting tension that the barbed suture imparts on the tissue for either closing a wound or fixing a prosthetic device to the tissue.

At present, there are no devices that are specifically designed for aligning and tensioning barbed sutures. Thus, in spite of the above advances, there remains a need for systems, devices, and methods for properly aligning and tensioning barbed sutures in tissue and prosthetic devices. There also remains a need for a device that acts as a guide for the proper placement of barbed sutures, as well as a need for a device that provides sufficient visual access to surgical sites where barbed sutures are used.

SUMMARY OF THE INVENTION

In one embodiment, a device for tensioning barbed sutures includes a shaft having a proximal end and a distal end with a pressure applying surface, and a handle connected with the proximal end of the shaft. The device desirably includes at least one groove extending through the shaft from the pressure applying surface at the distal end of the shaft toward the proximal end of the shaft. The groove is adapted to allow for efficient alignment of the barbed suture in the shaft of the device, as well as applying a desired level of tension to the barbed suture.

In one embodiment, the handle is offset from the shaft so that the distal end of the shaft may be easily seen when the distal end is positioned at a surgical site. In one preferred embodiment, the shaft has a first longitudinal axis and the handle has a second longitudinal axis that is offset from the first longitudinal axis so as to provide visual access to the distal end of the shaft when the shaft is positioned at a surgical site. The distal end of the shaft may be tapered to provide more visibility of the surgical site. In one embodiment, the height of the shaft is tapered so that the distal end of the shaft has a smaller height than an intermediate section of the shaft.

The at least one groove in the shaft is adapted to receive at least one section of a barbed suture therein. The at least one groove may include a pair of aligned grooves. The aligned grooves may extend side-by-side and may be substantially parallel to one another, whereby each of the aligned grooves is adapted to receive a section of a barbed suture. The device may also include one or pledgets. Each of the pledgets may have a pair of openings, whereby the spacing between the pair of grooves extending through the shaft matches the spacing between the pair of openings in the pledget. In other embodiments, the pledget may have only one opening, or may have more than two openings.

The tensioning device may be made of materials such as metals and polymers. In one embodiment, the tensioning device may be made of metal, metal alloys, stainless steel, and titanium. In one embodiment, the tensioning device may be made of polymeric materials such as polypropylene, polyethylene, polyvinylchloride, and polystyrene.

In one embodiment, the device preferably includes a tension gauge coupled with the shaft for selecting and controlling the tension level applied to barbed sutures. The tension gauge preferably enables operators to select a preferred tension level and to apply the preferred tension level to the barbed suture so as to avoid breaking the suture and/or avoid the above-described medical problems that may result from over-tensioning sutures. The device may also include a tensioning clamp in communication with the tension gauge for engaging the barbed suture in the at least one groove. In one embodiment, the tensioning clamp is adapted for pulling or urging the barbed suture toward the proximal end of the shaft so as to apply tension to the barbed suture. The tensioning clamp preferably stops applying additional tension to the suture once the pre-selected tension level has been achieved. At that stage, the tensioning clamp may disengage from contacting the barbed suture. The device may also include a tensioning lever or trigger interconnected with the tensioning clamp and being accessible at the handle. In one embodiment, the tensioning lever or trigger is desirably pulled one or more times for applying tension on the barbed suture through the tensioning clamp.

In one embodiment, the device preferably includes a cutting assembly coupled with the shaft for cutting the barbed suture. The cutting assembly is preferably activated after the predetermined tension level has been applied to the barbed suture. The cutting assembly may include a cutting knife or blade that intersects the shaft for cutting the barbed suture extending along the shaft. In one embodiment, the cutting assembly is interconnected with the tensioning lever so that the cutting knife is advanced by pulling on the tensioning lever. In one embodiment, the cutting knife is not activated until the pre-selected tension level has been applied to the suture.

In one embodiment, a device for tensioning barbed sutures includes a handle, and a shaft having a proximal end connected with the handle and a distal end remote therefrom, whereby the distal end of the shaft includes a pressure applying surface. The device desirably includes a pair of grooves extending through the shaft from the pressure applying surface at the distal end of the shaft toward the proximal end of the shaft, whereby a first one of the grooves is adapted to receive a first section of a barbed suture and a second one of the grooves is adapted to receive a second section of the barbed suture. The shaft may have a first longitudinal axis and the handle may have a second longitudinal axis that is offset from the first longitudinal axis so as to provide visual access to the distal end of the shaft. In one embodiment, the pressure applying surface at the distal end of the shaft lies is a plane that traverses the first longitudinal axis of the shaft.

In one embodiment, a device for tensioning barbed sutures includes a handle, a shaft having a proximal end connected with the handle and a distal end remote therefrom, whereby the distal end of the shaft includes a pressure applying surface. The device desirably includes a pair of grooves extending through the shaft from the pressure applying surface at the distal end of the shaft toward the proximal end of the shaft. A barbed suture may be tensioned using the device. In one embodiment, a first section of the barbed suture extends through a first one of the grooves and a second section of the barbed suture extends through a second one of the grooves. The barbed suture may be a bidirectional barbed suture having a first section having first barbs extending in a first axial direction and a second section having second barbs extending in a second axial direction that is away from the first axial direction.

These and other preferred embodiments of the present invention will be described in more detail below.

BRIEF DESCRIPTION OF THE DRAWING

FIGS. 4A-4C show a method of securing a prosthetic device to tissue using barbed sutures, in accordance with one embodiment of the present invention.

DETAILED DESCRIPTION

Figure 1A:
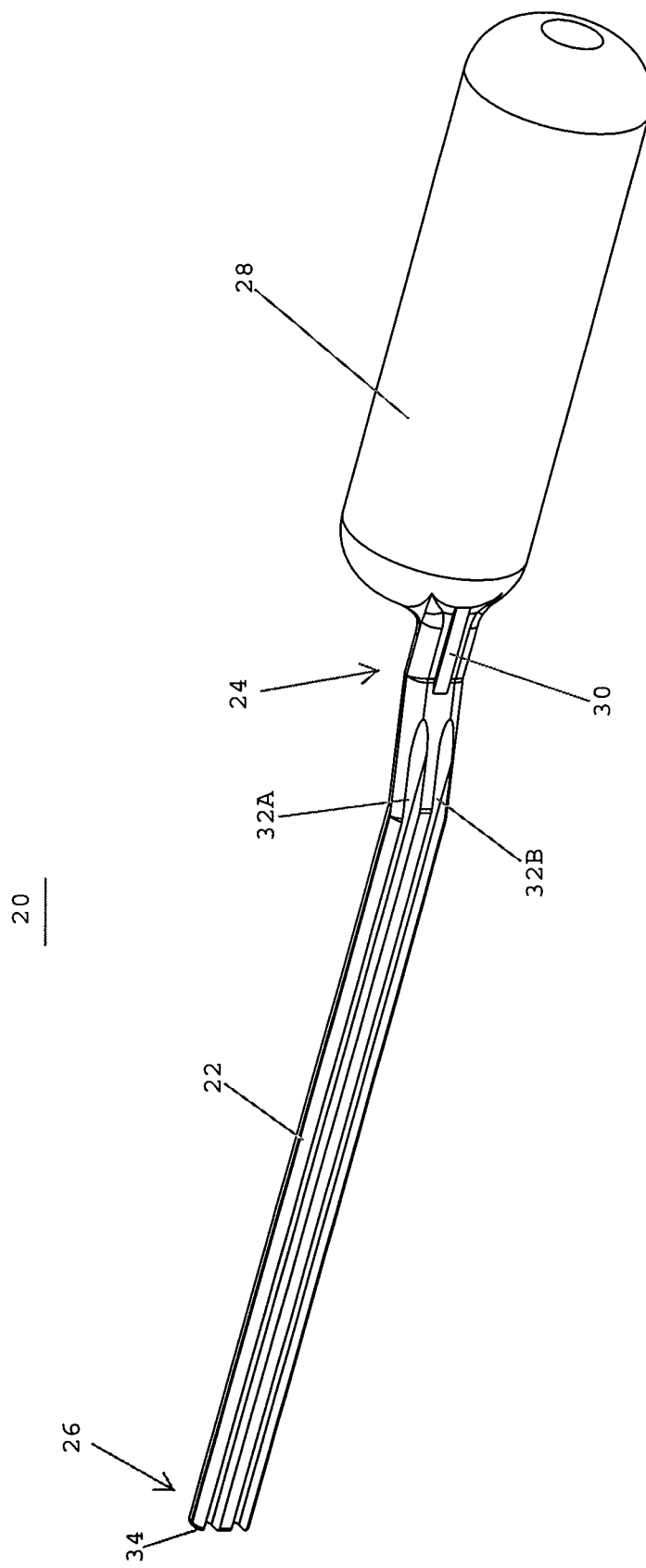
FIG. 1A shows a perspective view of a device for tensioning barbed sutures, in accordance with one embodiment of the present invention.

Referring to FIG. 1A, in one embodiment, a device 20 for tensioning barbed sutures includes a shaft 22 having a proximal end 24 and a distal end 26. The device 20 also includes a handle 28 that is connected with the proximal end 24 of the shaft 22. The device 20 includes a reinforcing rib 30 that reinforces the structural integrity of the shaft and the connection of the shaft 22 with the handle 28. The device also preferably includes first and second grooves 32 A, 32 B that extend between the proximal end 24 and the distal end 26 of the shaft 22. The grooves 32 A, 32 B are preferably adapted to receive barbed sutures. The grooves 32 A, 32 B preferably align the barbed sutures in the respective grooves. The distal end 26 of the shaft 22 includes a pressure applying surface 34, which is typically perpendicular to the longitudinal axis of the shaft. The pressure applying surface 34 is preferably located at a distal-most end of the shaft 22. After the sections of the barbed sutures have been passed through tissue or a prosthetic device, and positioned within the grooves 32 A, 32 B, the pressure applying surface is desirably pressed against the tissue or the prosthetic device for applying pressure thereto. As pressure is applied using the pressure applying surface, proximal ends of the barbed suture may be pulled toward the proximal end of the shaft for applying tension to the suture.

Figure 1B:
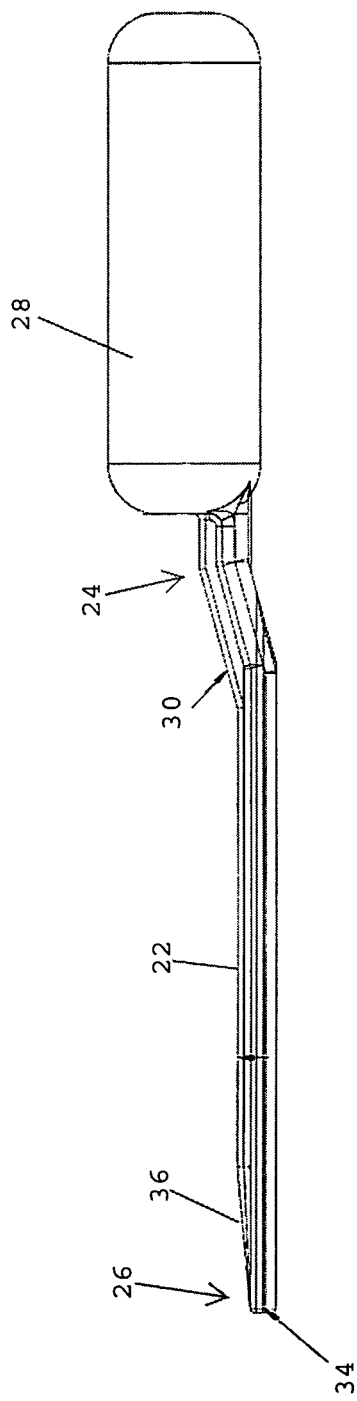
FIG. 1B shows a front elevational view of the device shown in FIG. 1A.

Referring to FIG. 1B, the handle 28 is preferably offset from the longitudinal axis of the shaft 22 to provide visibility of the distal end 26 of the shaft. The pressure applying surface 34 preferably lies in a plane that crosses the longitudinal axis of the shaft 22. The distal end 26 of the shaft 22 preferably also includes a tapered region 36 that provides additional visibility of the distal end 26 of the shaft. The reinforcing rib 30 enhances the structural integrity of the shaft, including the connection between the proximal end 24 of the shaft and the handle 28.

Figure 1C:
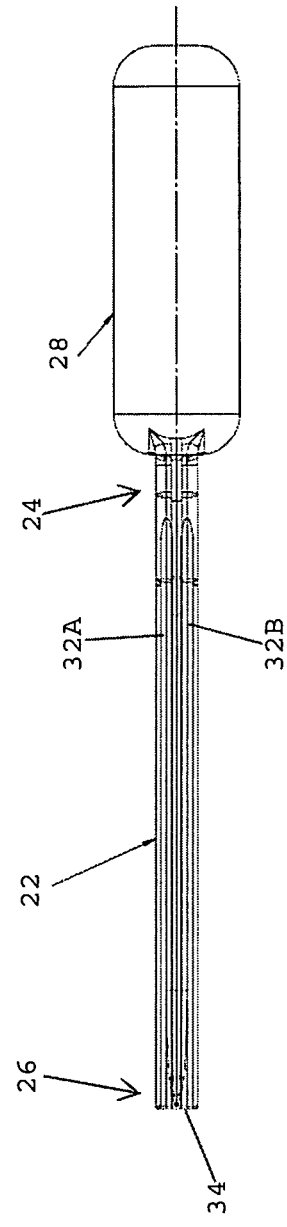
FIG. 1C shows a top plan view of the device shown in FIG. 1A.

Referring to FIG. 1C, the respective grooves 32A, 32B desirably extend from the distal end 26 of the shaft 22 toward the proximal end 24 of the shaft. In highly preferred embodiments, the distal ends of the grooves 32A, 32B begin at the pressure applying surface 34 and extend most of the way toward the proximal end 24 of the shaft. In other embodiments, the grooves may extend the entire length of the shaft. In still other embodiments, the grooves may extend only part of the way from the distal end of the shaft to the proximal end of the shaft. Referring to FIG. 1B, when viewed from the side, the longitudinal axis of the shaft 22 is offset from the longitudinal axis of the handle 28. When viewed from the top, as shown in FIG. 1C, the longitudinal axis of the shaft 22 is in substantial alignment with the longitudinal axis of the handle 28.

Figure 2:
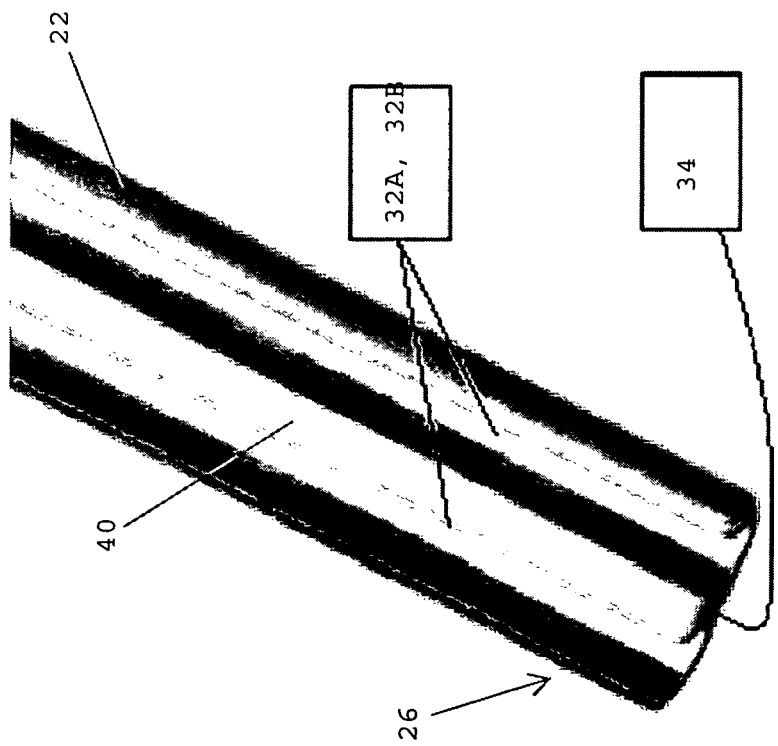
FIG. 2 shows a perspective view of a distal end of the device shown in FIG. 1A.

FIG. 2 shows the distal end 26 of the shaft 22. The distal end 26 of the shaft includes the pressure applying surface 34 that is adapted to apply pressure on tissue or prosthetic devices. The shaft 22 includes the pair of grooves 32A, 32B that are in communication with and extend from the pressure applying surface 34. The shaft 22 also includes a central projection 40 that divides the two grooves from one another. The central projection 40 preferably reinforces the structural integrity of the shaft 22. The grooves 32A, 32B preferably extend along respective longitudinal axes that are substantially parallel with one another. As such, the pair of grooves 32A, 32B may be used to align two barbed sutures next to one another, or two different sections of a barbed suture next to one another.

Figure 3A:
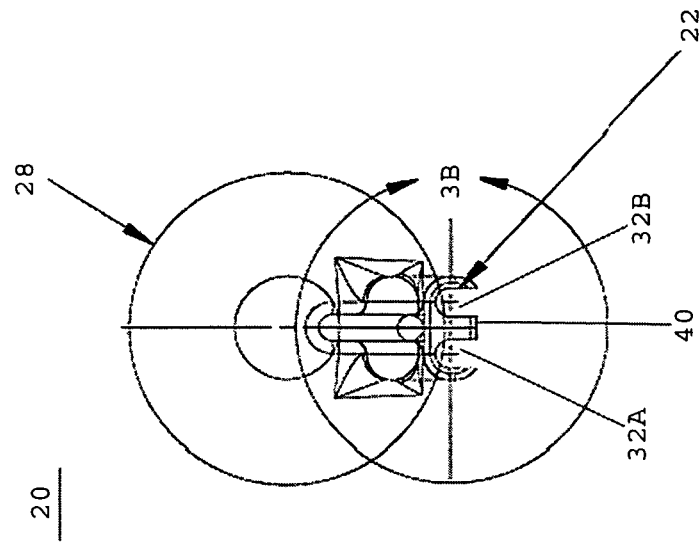
FIG. 3A shows an end view of the device shown in FIG. 1A.

FIG. 3A shows a distal end view of the tensioning device 20. As shown in FIG. 3A, the device 20 includes the handle 28 and the shaft 22 connected to the handle. The shaft 22 includes the first groove 32A, the second groove 32B and the projection 40 separating the grooves from one another. The longitudinal axis of the handle 28 is desirably offset from the longitudinal axis of the shaft 22 to provide visual access to the distal end of the shaft.

Figure 3B:
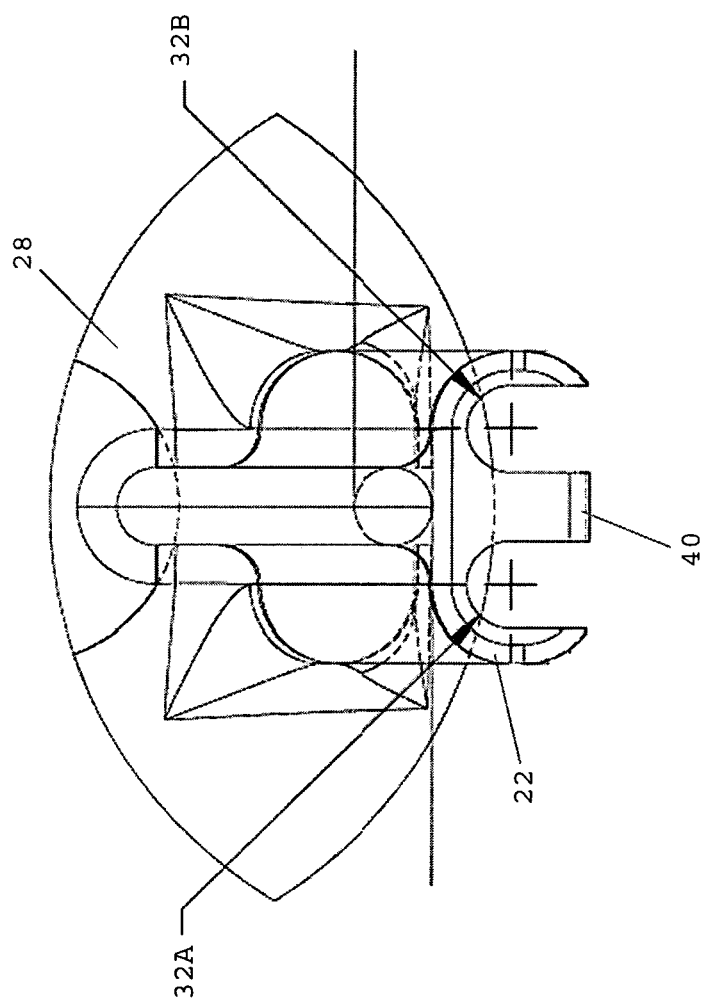
FIG. 3B shows an expanded view of a portion FIG. 3A.

Referring to FIG. 3B, the pair of grooves 32A, 32B are preferably in alignment with one another and preferably extend to the distal-most end of the shaft 22. The proximal end of the shaft 22 is connected to the handle 28. As shown above, the distal end of the shaft 22 is visible due to it being offset from the longitudinal axis of the handle 28. As will be described in more detail below, a first barbed suture is preferably aligned and tensioned using the first groove 32A, and a second barbed suture is preferably aligned and tensioned using the second groove 32B.

In one embodiment, the device has an overall length of about 6-7 inches, and more preferably about 6.5 inches, a handle having a length of about 2-3 inches, and more preferably about 2.5 inches, and a shaft having a length of about 3-5 inches, and more preferably about 4.0 inches. In one preferred embodiment, the longitudinal axis of the shaft is offset from the longitudinal axis of the handle by about 0.20-0.30 inches, and more preferably about 0.25-0.27 inches, and even more preferably about 0.263 inches. The distal end of the shaft preferably has a thickness of about 0.125 and a width of about 0.25 inches. The grooves are preferably about 0.075 inches wide and are spaced from one another by about 0.055 inches. The bottoms of the grooves preferably have a radius of about 0.035 inches. Each of the grooves preferably has a center, and the centers of the grooves are spaced about 0.125 inches from one another. The central projection extending between the grooves had a width of about 0.055 inches. The above-described dimensions are merely exemplary in nature and may be readily modified and still fall within the scope of the present invention. For example, the dimensions of a device may be modified to accommodate barbed sutures having different dimension, or to accommodate different surgical techniques/conditions or different prosthetic devices.

In one embodiment, the tensioning device is preferably made of a polymeric or metallic material, and is more preferably made of a polymeric material formed using injection molding techniques. Preferred polymeric materials for the tensioning device may include polypropylene, polyethylene, polyvinylchloride, or polystyrene. Preferred metals may include metal alloys such as stainless steel and titanium.

Referring to FIGS. 4A-4C, in one embodiment, the tensioning device 20 shown and described herein is used to secure a prosthetic device in place, such as a prosthetic heart valve having a valve sewing ring 46, and to apply tension to the barbed sutures that are passed through the valve sewing ring 46. As shown in FIG. 4A, a bidirectional barbed suture 44 includes a first section 48 having a first set of barbs 50 and a first suture needle 52, and a second section 54 having a second set of barbs 56 and a second suture needle 58. The barbs of the first set of barbs 50 extend in a different direction than the barbs of the second set of barbs 56. The bidirectional barbed suture includes a pledget 60 having first and second openings 62A, 62B. In one embodiment, the first suture needle 52 is passed through the first opening 62A of the pledget 60 and the second suture needle 58 passed through the second opening 62B of the pledget 60. The pledget 60 is preferably positioned between the first set of barbs 50 and the second set of barbs 56.

Referring to FIGS. 4A-4C, the first suture needle 52 is pulled through tissue T and the valve sewing ring 46 so that some of the first barbs 50 extend from the top surface 66 of the valve sewing ring 46. The second suture needle 58 is pulled through the tissue T and the valve sewing ring 46 so that some of the second barbs 56 extend from the top surface 66 of the valve sewing ring 46. Referring to FIG. 4B, the above described steps may be repeated around the perimeter of the valve sewing ring 46 for effectively securing the heart valve 45 to the tissue T. Referring to FIG. 4C, in one embodiment, the first and second sections 48, 54 of each bidirectional suture preferably extend along axes that are substantially parallel with one another. In one embodiment, the spacing between the first and second sections 48, 54 of the suture is controlled by the spacing between the openings 62A, 62B in the pledget 60. The spacing between the first and second sections 48, 54 of the suture may generally match the spacing between the openings 62A, 62B of the pledget 60.

Figure 5A:
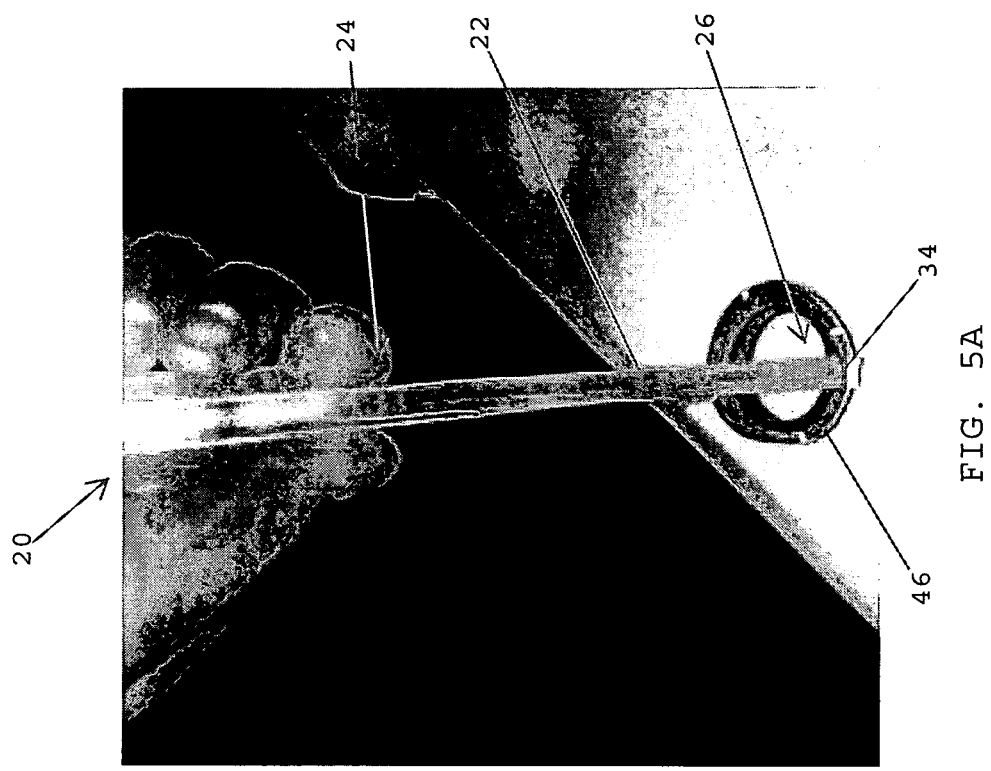
FIGS. 5A-5B show a method of tensioning a barbed suture using the device shown in FIG. 1A.

Referring to FIG. 5A, in order to apply tension to the bidirectional barbed suture 44 shown in FIG. 4, the tensioning device 20 shown and described herein is used. The first and second sections 48, 54 of the bidirectional barbed suture are placed in the respective grooves 32A, 32B of the shaft 22. The pressure applying surface 34 at the distal end 26 of the shaft 22 is desirably pressed against the top surface of the sewing ring 46 to apply pressure to the sewing ring. As pressure is applied to the sewing ring by the pressure applying surface 34, the proximal ends of the bidirectional barbed suture are pulled toward the proximal end 24 of the shaft 22 so as to apply tension to the structure. As the bidirectional barbed suture is pulled toward the proximal end 24, the barbs on the first and second barbed sections 50, 56 pass through the top surface 66 of the sewing ring 46 to secure the sewing to a substrate such as a heart valve or tissue.

Figure 5B:
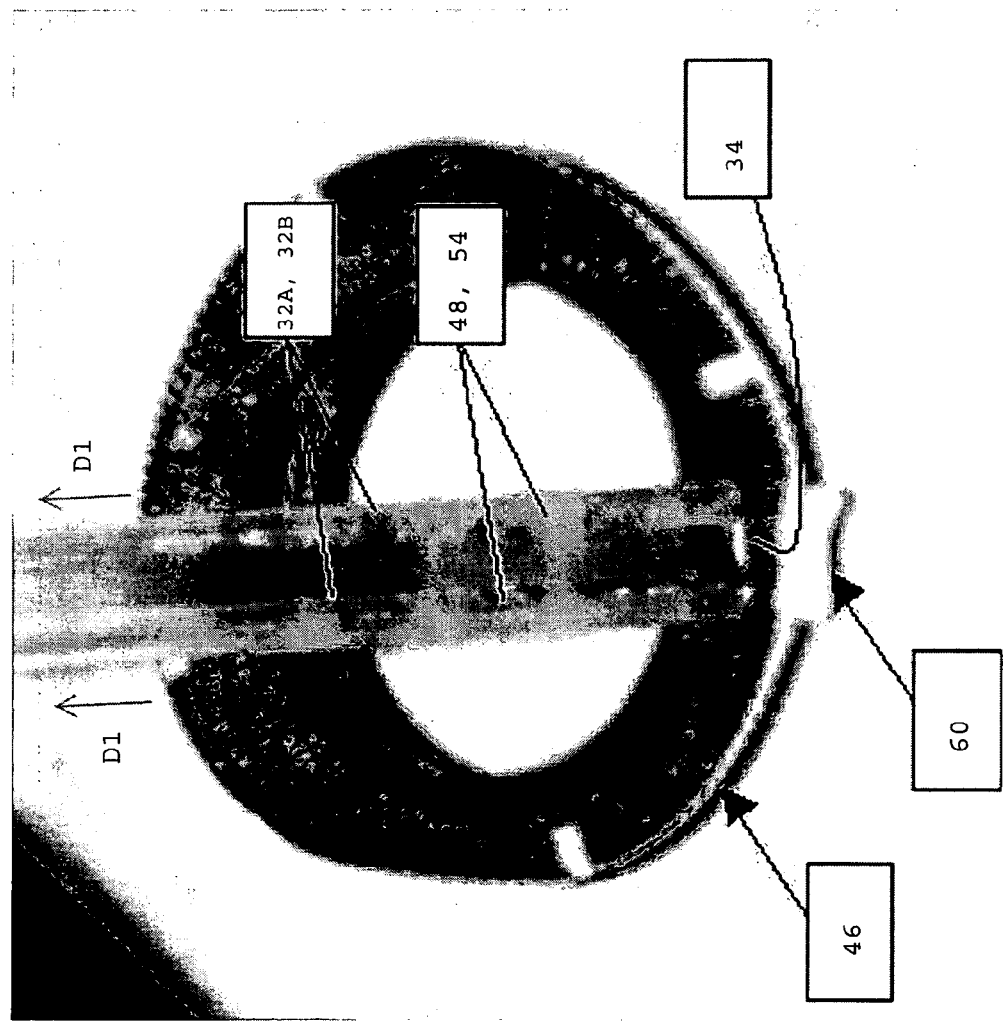

Referring to FIG. 5B, the first and second sections 48, 54 of the bidirectional barbed suture preferably extend through the first and second grooves 32A, 32B of the shaft 22 as the first and second barbed sections 48, 54 are pulled toward the proximal end of the shaft 22 in the direction indicated by the arrow designated $D_1$, the pressure applying surface 34 is pressed against the top surface of the valve sewing ring 46. Although the present invention is not limited by any particular theory of operation, it is believed that the structure shown and described herein provides highly localized pressure on tissue or prosthetic devices where needed for tensioning barbed sutures. Thus, the tissue will not be stretched as discussed above and a more secure anchoring of the suture will occur. Moreover, the present invention provides visibility at the distal end of the tensioning device for observing the surgical area. In addition, the present invention provides an integrated tool that enables barbed sutures to be properly secured to tissue and/or prosthetic devices such as heart valves having sewing rings, thereby obviating the need to use multiple tools such as surgical forceps or bulky items such as finger tips.

Figure 6A:
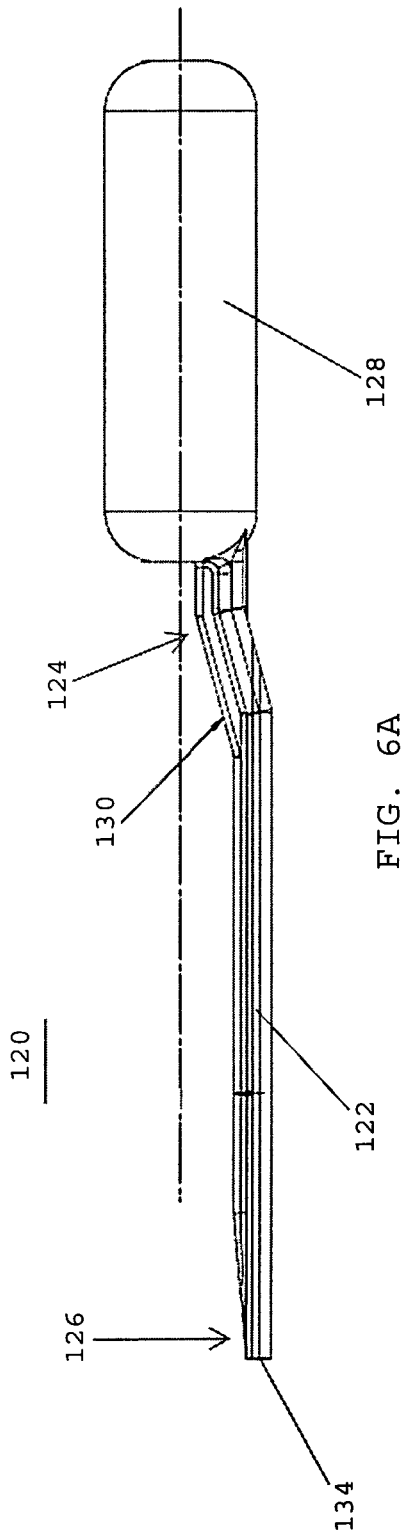
FIG. 6A shows a front elevational view of a device for tensioning barbed sutures, in accordance with one embodiment of the present invention.
Figure 6B:
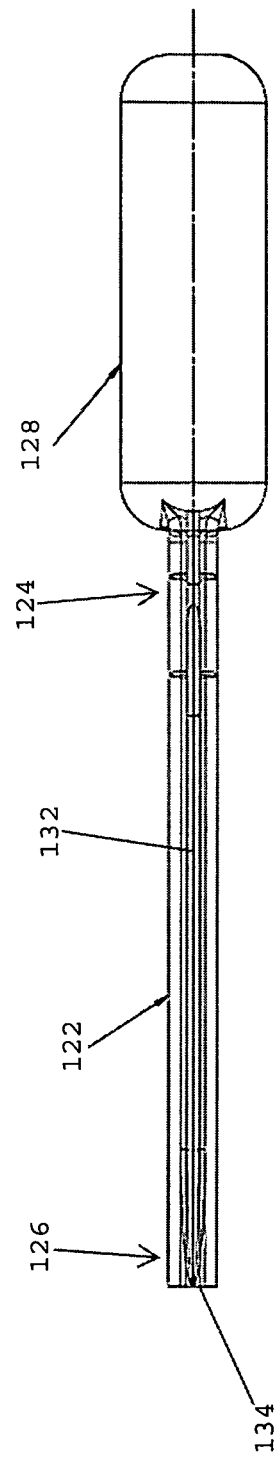
FIG. 6B shows a top plan view of the device shown in FIG. 6A.

Referring to FIGS. 6A and 6B, in one embodiment, a device 120 for tensioning sutures includes a shaft 122 having a proximal end 124 and a distal end 126. The proximal end 124 of the shaft 122 is secured to a handle 128. The shaft 122 includes a reinforcing rib 130 that provides structural integrity for the shaft. Referring to FIG. 6B, the shaft 122 includes a groove 132 that extends from the distal end 126 of the shaft toward the proximal end 124 of the shaft. Referring to FIGS. 6A and 6B, the distal end 126 of the shaft includes a pressure applying surface 134 that is adapted to apply pressure to tissue and/or prosthetic devices when tensioning barbed sutures.

Figure 7B:
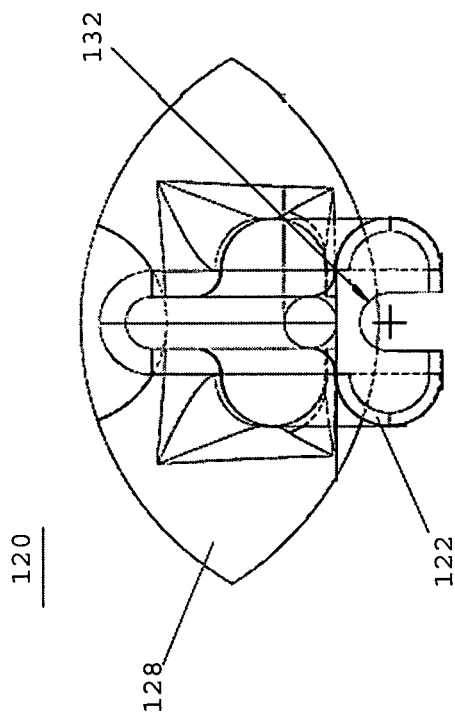
FIG. 7B shows an expanded view of a portion of FIG. 7A.
Figure 7A:
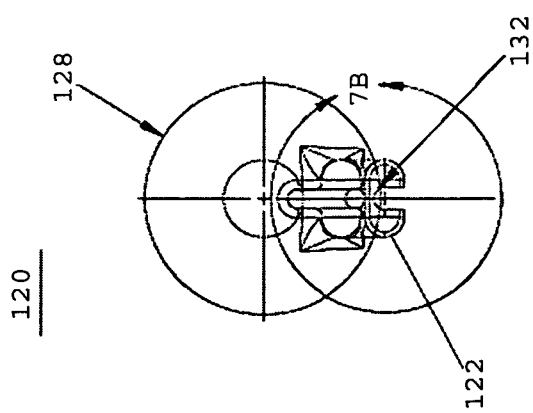
FIG. 7A shows an end view of the device shown in FIG. 6A.

Referring to FIGS. 7A and 7B, the single groove 132 extends to the distal-most end of the device 120. The handle 128 has a longitudinal axis that is preferably offset from the longitudinal axis of the shaft 122 so that the distal-most end of the tensioning device may be observed during a surgical procedure. The single groove provides a device that is smaller at the distal end thereof so as to provide more room at a surgical site. A tensioning device having a single groove may also be provided for instances wherein only one leg of a barbed suture is to be tensioned at any one time.

Figure 8A:
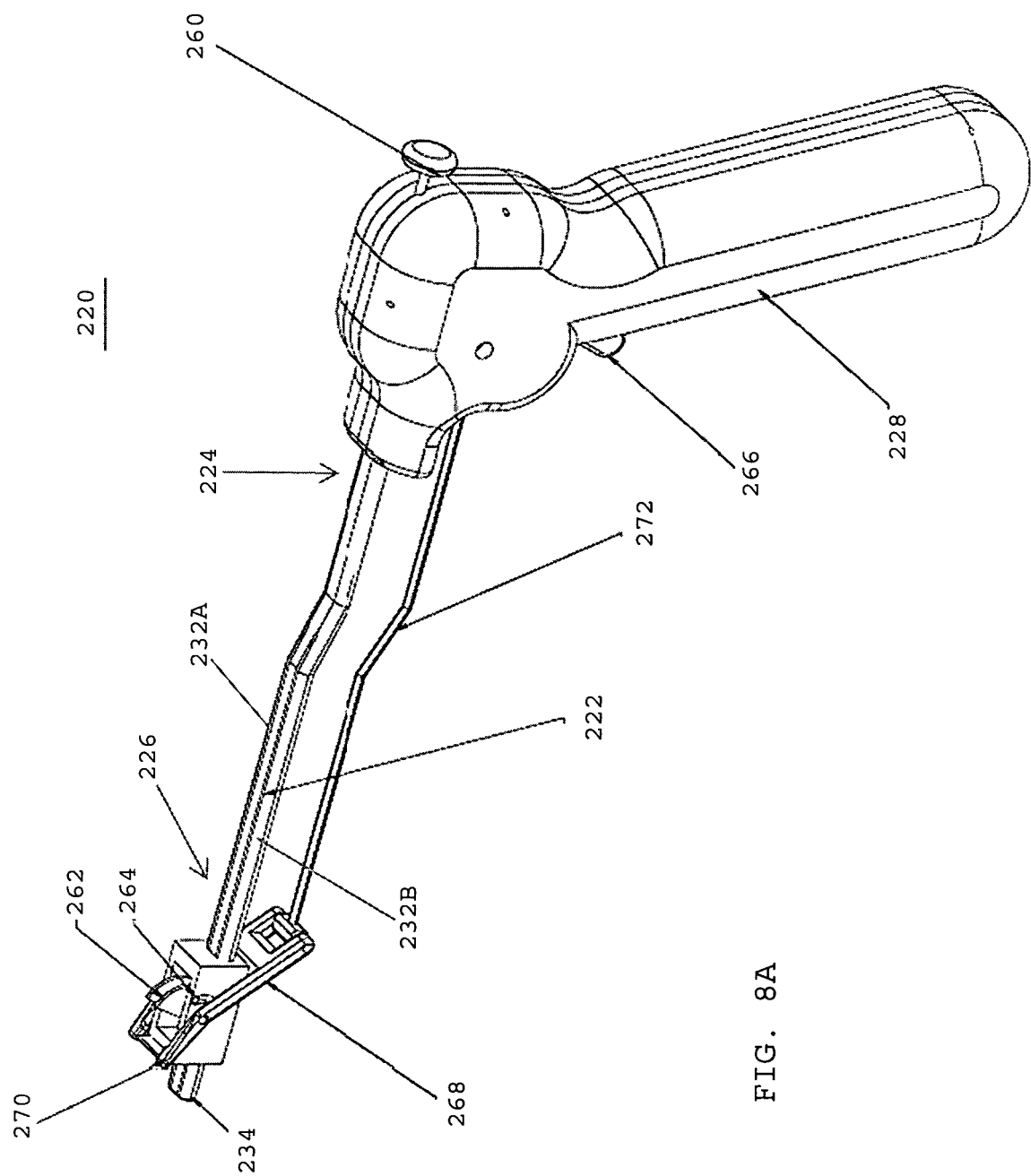
FIG. 8A shows a perspective view of a device for tensioning barbed sutures, in accordance with one embodiment of the present invention.
Figure 8B:
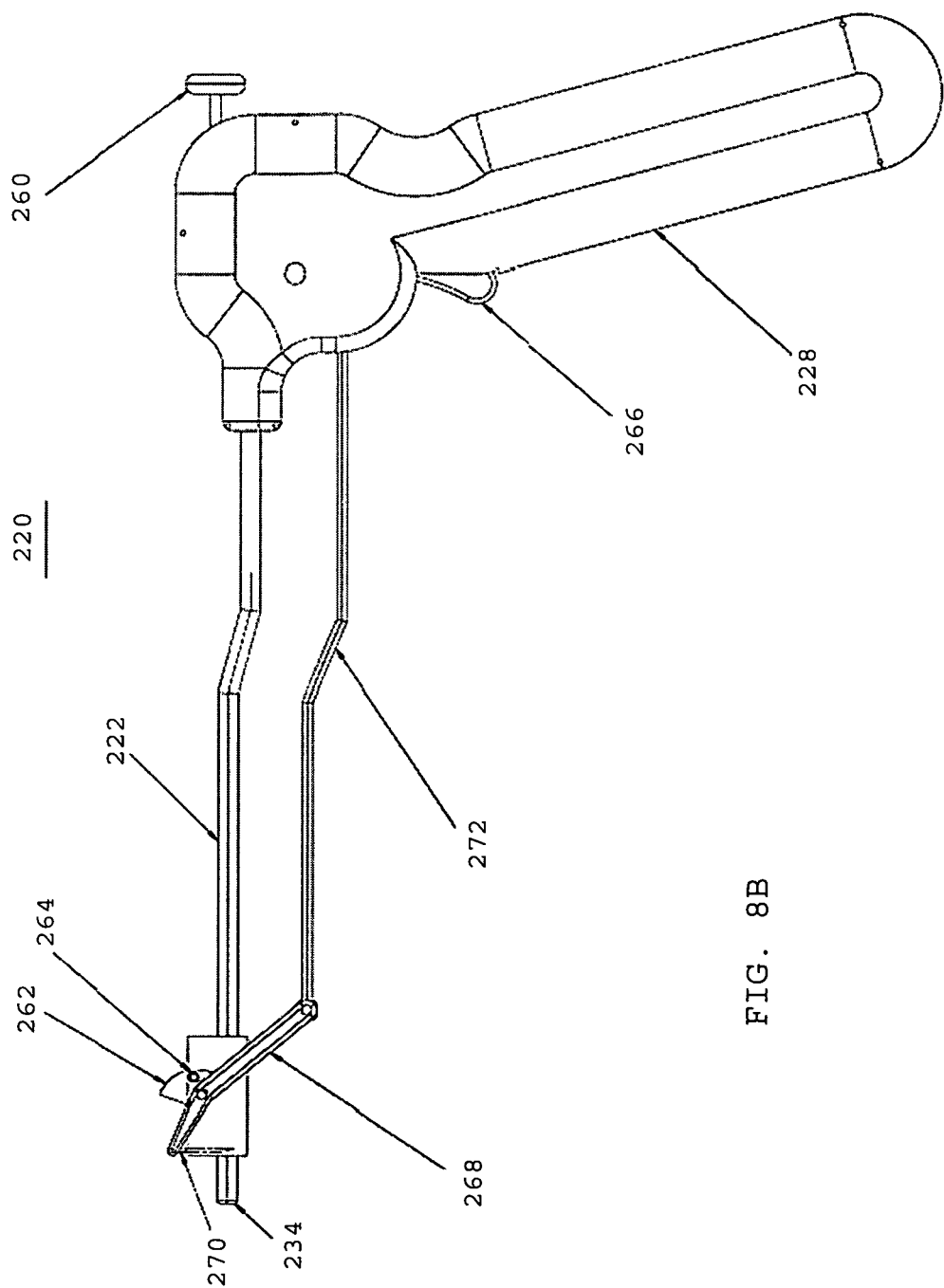
FIG. 8B shows a front elevational view of the device shown in FIG. 8A.

Referring to FIGS. 8A and 8B, in one embodiment, a device 220 for automatically tensioning and cutting barbed sutures includes a shaft 222 having a proximal end 224 and a distal end 226. The device 220 includes a handle 228 connected to the proximal end 224 of the shaft 222. The shaft 222 preferably includes a pair of side-by-side grooves 232A, 232B that are substantially similar to the grooves shown and described above in the embodiment associated with FIG. 1A. The device 220 also desirably includes a pressure applying surface 234 provided at the distal end 226 of the shaft 222 for applying pressure to tissue and/or prosthetic devices such as heart valves. As is known to those skilled in the art, conventional heart valves may include a valve sewing ring that is used for securing the heart valve in place.

The device 220 preferably has a tensioning assembly that is used to select and control the level of tension that is applied to a barbed suture, and a cutting assembly that cuts the barbed suture after the desired tension level has been applied to the barbed suture. In one embodiment, the tensioning assembly preferably includes a tension selection knob 260 for selecting a tension level, a tension applying clamp 262 that is interconnected with the tension selection knob 260, a suture cam adjustment and rotary stop 264 that is interconnected with the tension applying clamp 262, and a trigger 266 provided on the handle 228. The device 220 also desirably includes a cutting assembly 268 having a cutting knife 270 and a connecting rod 272 coupled with the cutting knife 270. The proximal end of the connecting rod is coupled with the trigger 266.

In one embodiment, the proximal ends of a barbed suture, such as a bidirectional barbed suture, are aligned in the side-by-side grooves 232A, 232B extending through the shaft 222. The tension selection knob 260 is used to select a desired tension level to be applied to the barbed suture. Once the desired tension level is selected, the trigger 266 may be pulled one or more times for applying tension to the barbed suture through the tension applying clamp 262. Each time the trigger 266 is pulled, the tension applying clamp 262 preferably engages the barbed suture and pulls or urges the barbed suture toward the proximal end 224 of the shaft 222. The barbed suture may advance proximally by a certain distance each time the trigger 266 is pulled. Once the predetermined tension level is reached, the suture cam adjustment and rotary stop 264 will adjust the position of the tension applying clamp 262 so that the clamp will no longer apply additional tension to the barbed suture. At that point, the trigger 266 may be pulled again for pivoting the cutting knife 270 downwardly for cutting the suture to a predetermined length. The device may include an internal switch that deactivates the tension applying assembly and activates the cutting assembly after the pre-selected tension level has been attained. In other embodiments, the device may have only one groove, or may have more than two grooves.

Although the present invention is not limited by any particular theory of operation, it is believed that the device disclosed herein enables medical personnel to apply tension to a suture while also applying pressure against tissue or a prosthetic device that is to be secured in place using the suture. Moreover, the tensioning device disclosed herein enables the suture to be properly aligned over the tissue or prosthetic device. The tensioning device disclosed herein also facilitates the application of barbed fasteners into tissue or prosthetic devices. The present device also provides greater visibility of the surgical site where the barbed fastener is anchored. This greater visibility is particularly useful in valve replacement and annuloplasty procedures. In one embodiment, the greater visibility is provided by offsetting the longitudinal axis of the handle from the longitudinal axis of the shaft used to apply tension and align the suture. The present invention also provides for precise alignment of barbed sutures relative to their preferred spacing in the tissue. In one embodiment, this is obtained by providing two or more grooves extending through the shaft of the tensioning device, whereby the spacing between the grooves matches the spacing between the openings in a pledget.

In one embodiment, the present invention discloses a device used to tension barbed sutures. The device preferably has a handle that is offset from the shaft, which provides for enhanced ergonomics as well as allowing the surgeon to have direct visual access to the distal end of the shaft. Improved visual access is particularly important when working in a deep cavity such as during valve replacement and annuloplasty procedures. In one embodiment, the device has a pair of grooves or channels that run the length of the shaft. The grooves serve as guides for the barbed suture when tension is applied to the proximal end of the suture strands. The grooves are not required to extend the full length of the shaft and may be located only at the distal end of the shaft. In some embodiments, an optional shaft extension may be used to engage tissue or a prosthetic device.

In one embodiment, the grooves extending through the shaft are designed to hold the barbed suture in place. In one embodiment, there may be only one groove that enables a surgeon to tension one suture at a time. The width and the depth of the grooves extending through the shaft may be altered so as to fit the size of the suture being used.

In one embodiment, the sutures are placed in the grooves. While tension is applied to the proximal ends of the sutures, the distal end of the device is pressed against tissue or prosthetic devices such as a sewing ring. In one embodiment, the spacing between the side-by-side grooves matches the spacing of the openings in a pledget, which determines how far apart the sutures are spaced from one another as the sutures emerge from the sewing ring.

In one embodiment, the barbed suture is made using a non-absorbable polymeric material, and a non-absorbable multi-filament polyester suture, commonly sold under the trademark Ethibond Excel by Ethicon, Inc., with surgical needles attached to both ends of the suture. A Teflon pledget may be positioned in the middle of the polymeric anchoring section. The barbs on the barbed suture are preferably bidirectional with a first section having barbs extending in one direction and a second section having barbs extending in another direction.

In one embodiment, the tensioning device may include a force gauge or force indicator incorporated into the device. The force gauge may be located at or near the handle of the device to allow an operator to precisely set a tension level to be applied to the suture. In this embodiment, the tensioning gauge enables a more consistent level of tension to be applied to the suture, which may be particularly useful for laparoscopic or minimally invasive procedures where a surgeon's sight and tactile feel are limited.

In one embodiment, a device for tensioning barbed sutures may include a mechanism to enable tensioning of barbed fixation devices by feeding the proximal ends of the barbed device through a mechanism that will allow the fixation device to advance in a proximal direction only. The tensioning device may include a ratcheting mechanism to provide for a predetermined incremental advancement of the suture. The tensioning mechanism may also release or free the proximal end of the barbed fixation device, particularly when a predetermined tension level has been achieved.

In one embodiment, the tensioning device may include a shaft having an end that is adapted to accommodate multiple grooves to guide multiple sutures while simultaneously making contact of the distal end of the shaft with the tissue or prosthetic device. In one embodiment, the shaft ends may include shapes with multiple prongs with each prong having a groove that extends from its distal end to at least part way toward the proximal end of the shaft. This particular configuration may be well suited for use when it is desirable to secure large prosthetic devices, such as surgical mesh to tissue.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A device for tensioning barbed sutures comprising:
   a shaft having a proximal end, a distal end, and a longitudinal axis extending between the proximal and distal ends;
   a handle connected with the proximal end of said shaft;
   the distal end of said shaft including a pressure applying surface located at a distal-most end of said shaft that lies in a plane that crosses the longitudinal axis of said shaft, wherein the pressure applying surface is perpendicular to the longitudinal axis of said shaft, and wherein the distal end of said shaft has first and second major surfaces;
   a pair of aligned open grooves extending through said shaft from the pressure applying surface at the distal end of said shaft toward the proximal end of said shaft, wherein said pair of aligned open grooves extend side-by-side and in a common plane along the longitudinal axis of said shaft, wherein said pair of open grooves are open at said first major surface and face in the same direction, and wherein said device further comprises a central projection dividing said pair of open grooves from one another.

2. The device as claimed in claim 1, wherein said handle has a second longitudinal axis that is offset from the first longitudinal axis of said shaft.

3. The device as claimed in claim 1, wherein each said open groove is adapted to receive a section of a barbed suture therein.

4. The device as claimed in claim 1, wherein said central projection dividing said open grooves from one another has an elongated surface that defines said first major surface of said shaft.

5. The device as claimed in claim 1, wherein said device comprises a material selected from the group consisting of metal, metal alloys, stainless steel, and titanium.

6. The device as claimed in claim 1, wherein said device comprises polymeric materials selected from the group consisting of polypropylene, polyethylene, polyvinylchloride, and polystyrene.

7. The device as claimed in claim 1, wherein said pressure applying surface at the distal-most end of said shaft comprises a flat surface that extends across a width of said shaft at the distal-most end of said shaft.

8. The device as claimed in claim 1, wherein each of said grooves has a bottom with a concave surface having a radius.

9. The device as claimed in claim 8, wherein said bottoms define closed ends of said grooves.

10. A device for tensioning barbed sutures comprising:
    a handle;
    a shaft having a proximal end connected with said handle, a distal end remote therefrom, and a longitudinal axis extending between the proximal and distal ends, wherein the distal end of said shaft includes a pressure applying surface located at a distal-most end of said shaft that lies in a plane that crosses the longitudinal axis of said shaft and that is perpendicular to the longitudinal axis of said shaft, and wherein the distal end of said shaft has first and second major surfaces;
    a pair of open grooves extending through said shaft from the pressure applying surface at the distal end of said shaft toward the proximal end of said shaft, wherein a first one of said open grooves is adapted to receive a first section of a barbed suture and a second one of said open grooves is adapted to receive a second section of the barbed suture, wherein said pair of open grooves extend side-by-side and lie in a common plane along the longitudinal axis of said shaft, wherein said pair of open grooves are open at said first major surface, closed at said second major surface, and face in the same direction at said first major surface, and wherein said device further comprises a central projection dividing said open grooves from one another.

11. The device as claimed in claim 10, wherein said handle has a second longitudinal axis that is offset from the first longitudinal axis so as to provide visual access to the distal end of said shaft.

12. The device as claimed in claim 11, wherein said pressure applying surface at the distal-most end of said shaft comprises a flat surface that extends across a width of said shaft at the distal-most end of said shaft.

13. The device as claimed in claim 10, wherein each of said grooves has a bottom with a concave surface having a radius.

14. A device comprising:
    a handle;
    a shaft having a proximal end connected with said handle, a distal end remote therefrom, and a longitudinal axis extending between the proximal and distal ends, wherein the distal end of said shaft includes a flat pressure applying surface that is perpendicular to the longitudinal axis of said shaft and that lies in a plane that extends across a distal-most end of said shaft, and wherein the distal end of said shaft has first and second major surfaces;

a pair of open grooves extending through said shaft from the pressure applying surface at the distal end of said shaft toward the proximal end of said shaft, wherein said pair of open grooves extend side-by-side and lie in a common plane along the longitudinal axis of said shaft, wherein said pair of open grooves are open at said first major surface and face in the same direction at said first major surface, and wherein said device further comprises a central projection dividing said open grooves from one another;

a barbed suture having a first section extending through a first one of said open grooves and a second section extending through a second one of said open grooves.

15. The device as claimed in claim 14, wherein said barbed suture is a bidirectional barbed suture with the first section having first barbs extending in a first axial direction and the second section having second barbs extending in a second axial direction that is away from the first axial direction.

16. The device as claimed in claim 15, further comprising a pledget having a pair of openings, wherein the spacing between said pair of open grooves extending through said shaft matches the spacing between said pair of openings in said pledget.

17. The device as claimed in claim 16, wherein said handle is offset from said shaft so as to provide visual access to the distal end of said shaft.

18. The device as claimed in claim 14, wherein said device comprises a material selected from the group consisting of metals and polymers.

19. The device as claimed in claim 14, wherein each of said grooves has a bottom with a concave surface having a radius.

* * * * *